United States Patent
Abel

(10) Patent No.: US 12,274,810 B2
(45) Date of Patent: Apr. 15, 2025

(54) METHODS, KITS AND COMPOSITIONS FOR NOVEL AGAROSE-BASED DERMAL FILLER WITH ENHANCED RHEOLOGICAL PROPERTIES PROVIDING SAFETY FEATURES

(71) Applicant: Advanced Aesthetic Technologies, Inc., Danvers, MA (US)

(72) Inventor: Douglas Abel, Wayne, PA (US)

(73) Assignee: Advanced Aesthetic Technologies, Inc., Brookline, MA (US)

( * ) Notice: Subject to any disclaimer, the term of this patent is extended or adjusted under 35 U.S.C. 154(b) by 1038 days.

(21) Appl. No.: 17/185,371

(22) Filed: Feb. 25, 2021

(65) Prior Publication Data

US 2021/0268144 A1    Sep. 2, 2021

Related U.S. Application Data

(60) Provisional application No. 62/982,982, filed on Feb. 28, 2020.

(51) Int. Cl.
| | | |
|---|---|---|
| *A61L 27/26* | (2006.01) | |
| *A61L 27/20* | (2006.01) | |
| *A61L 27/52* | (2006.01) | |
| *A61M 5/44* | (2006.01) | |

(52) U.S. Cl.
CPC ............... *A61L 27/26* (2013.01); *A61L 27/20* (2013.01); *A61L 27/52* (2013.01); *A61M 5/445* (2013.01); *A61L 2400/06* (2013.01); *A61L 2430/34* (2013.01); *A61M 2205/3382* (2013.01)

(58) Field of Classification Search
CPC .......... A61L 27/26; A61L 27/20; A61L 27/52; A61L 2400/06; A61L 2430/34; A61M 5/445; A61M 2205/3382
See application file for complete search history.

(56) References Cited

U.S. PATENT DOCUMENTS

| | | |
|---|---|---|
| 2010/0324531 A1 | 12/2010 | Heneveld et al. |
| 2016/0038635 A1 | 2/2016 | Matteuzzi |
| 2018/0368901 A1 | 12/2018 | Lee |
| 2020/0010577 A1 | 1/2020 | Burtt |
| 2020/0360619 A1 | 11/2020 | Prince |

FOREIGN PATENT DOCUMENTS

WO    2018231718 A1    12/2018

OTHER PUBLICATIONS

A. Scarano, F. Carinici, A. Piatelli. "Lip augmentation with a new filler (agarose gel): a 3-year follow-up study," Oral Surg Oral Med Oral Pathol Oral Radiol Endod 2009; 108: e11-e15. (Year: 2009).*
Product Summary of Algeness® , downloaded Feb. 6, 2024 from https://www.consultingroom.com/treatment/algeness; available online Oct. 31, 2016 (Year: 2016).*
A.P. Sclafani, S. Fagien. "Treatment of Injectable Soft Tissue Filler Complications," Dermatol Surg 2009; 35: 1672-1680 (Year: 2009).*
J. Commins. "Warming Injections Lowers Pain," downloaded Feb. 7, 2024 from https://www.healthleadersmedia. com/clinicalcare/warming-injections-lowers-pain; available on the internet Feb. 9, 2011. (Year: 2011).*
Invitation to Pay Additional Fees and, Where Applicable, Protest Fee issued in International Application No. PCT/US21/19675 dated May 10, 2021.
International Search Report and Written Opinion issued in International Application No. PCT/US2021/19675 dated Jul. 23, 2021.

* cited by examiner

*Primary Examiner* — Michael P Cohen
(74) *Attorney, Agent, or Firm* — WOMBLE BOND DICKINSO (US) LP; Deborah M. Vernon; Ricardo Joseph

(57) ABSTRACT

Disclosed herein are safe and effective ways to perform dermal filling procedures. Specifically, the present disclosure relates to agarose-based dermal fillers with advanced rheological properties which are easier to inject and disperse compared to HA based dermal fillers. The present disclosure further relates to the methods and kits to provide additional safety advantages over other injectables, as the agarose-based dermal fillers can be dispersed quickly to prevent injury to a patient.

36 Claims, 9 Drawing Sheets

METHODS, KITS AND COMPOSITIONS FOR NOVEL AGAROSE-BASED DERMAL FILLER WITH ENHANCED RHEOLOGICAL PROPERTIES PROVIDING SAFETY FEATURES

CROSS REFERENCE TO RELATED APPLICATION

This application claims benefit of priority to U.S. Provisional Application No. 62/982,982 filed Feb. 28, 2020, the contents of which are incorporated herein by reference in their entirety.

FIELD OF THE TECHNOLOGY

The present disclosure relates to agarose based-dermal filler compositions that is easily injectable and has improved rheological properties resulting in advanced dermal filling results as compared to commercial products utilizing hyaluronic acid (HA) technology, and methods of use thereof. The present disclosure further relates to kits and methods for correcting or modifying patient results during or after an agarose-based dermal filler procedure. In particular, the present disclosure is directed to rapidly and/or safely removing a misplaced injection, a lump or undesired pockets of injected agarose-based filler from a patient using saline (human injectable grade saline). The present disclosure also relates to kits that include novel range of agarose-based dermal fillers that have tunable/customizable rheological properties and instructions as to how the most appropriate agarose-based filler is selected for administration into a different target tissue of a subject.

BACKGROUND

The search for effective and safe tissue fillers has been an ongoing challenge in plastic and cosmetic surgery over recent decades. While hyaluronic acid (HA) based dermal fillers are the most popular degradable injectable products used for facial volumization, they have a risk of causing undesirable effects. HA dermal fillers are contraindicated in patients with known hypersensitivity to hyaluronic acid (or other components in the formulations such as crosslinking chemicals or other additives) and an active infection at the treatment site.

In addition, the placement or injection of conventional dermal fillers can also be problematic. While devastating complications are rare, to achieve the most desirable outcome (i.e., fuller appearance without lumps, and avoiding vascular problems) healthcare professionals (e.g., doctors, nurses, trained injectors) should have a thorough knowledge of facial anatomy and the potential danger areas, especially the distribution of the facial arteries and nerves so as to avoid injection into a blood vessel or to create a vascular compression blockage. Moreover, in addition to general facial anatomy, knowledge of any facial or dental surgeries of the specific patient is recommended to understand any areas of unusual vascular distribution.

When injecting a filler under a patient's skin, errors can occur, such as an unwanted pooling, collection, or pocket of the dermal filler. This pocket may result in a visual or tactile lump, unwanted by the patient. The pocket can also create unwanted and/or harmful compressive forces on vasculature. While pooling of a HA-based filler can be addressed through subsequent injections of hyaluronidase, the time to remove the HA-based filler may not be fast enough to address vascular problems. In addition, the pressure associated with injecting hyaluronidase may lead to additional problems for the vasculature.

Agarose is a biodegradable polymer, and the resemblance of this natural carbohydrate polymer to the extracellular matrix results in attractive features that bring about a strong interest in its usage in the dermal filler field. Like HA, agarose is a biocompatible polysaccharide that gives immediate and durable clinical results. It differs from HA in that it is stable in vivo and provides durable results after tissue implantation without the need for crosslinking chemicals or other additives.

SUMMARY

In one aspect, disclosed herein are safe and effective ways to perform dermal filling procedures. In various aspects and embodiments, the present disclosure helps to optimize aesthetic outcomes, safety and patient satisfaction through dispersing injected agarose-based fillers.

The dermal fillers of the present technology provide improved safety and/or implantation ease. Agarose based dermal fillers with advanced rheological properties disclosed herein are easier to inject and disperse. And if lumps or undesired pockets of injected agarose-based filler are discovered, the lumps/pockets can be easily removed from a patient using saline (human injectable grade saline). Moreover, if a clinician is unaware of a patient's specific facial vascular distribution, and an injection error is made, agarose-based fillers of the present disclosure can be easily dispersed with saline before permanent damage occurs.

In another aspect, provided herein is an agarose-based dermal filler composition with improved rheological properties that are suitable for dermal or soft tissue enhancement for cosmetic or therapeutic purposes are also disclosed herein.

Rheological properties relate to the ability of fillers to withstand different types of deformation and forces when implanted in various facial areas and planes. A better understanding of these rheological properties will guide clinicians in selecting the ideal filler for each region of the face based on pathology and the deformation forces acting in the area of interest. Therefore, selection of dermal filler with the right rheological properties is a key factor in achieving a natural-looking long-lasting desired aesthetic outcome.

A range of agarose-based dermal fillers with advanced rheological features with the aim to better predict its clinical behavior is lacking in conventional dermal fillers. The present disclosure delivers a solution for this need by providing novel agarose-based dermal fillers derived from an algal source that is CE-marked for use in Europe and for which North American clinical studies are anticipated.

In yet another aspect, the present disclosure is directed to agarose-based gel fillers that have tunable/customizable rheological properties. The rheological properties of this new filler can be carefully controlled and tailored to provide advanced dermal filling results as compared to commercial products utilizing HA technology.

In another aspect of the technology, the agarose-based gel fillers have been created to have a rheological that profile compatible with clinical behavior as a deep volumizer suitable for implantation in the subcutaneous or supraperiosteal tissue planes.

In another aspect, the agarose-based gel fillers have been customized to have a high elasticity to create and advanced volumizing effect.

In a further aspect, the agarose-based gel fillers have been formed to have a rheological profile designed to support a greater dispersing effect than HA based fillers. In some embodiments, the agarose-based gel fillers of the present technology were designed to be easily dispersed subcutaneously without the need for enzymes or other additives.

In one aspect, the present disclosure relates to a kit for performing a dermal filling procedure. The kit comprises a filler container containing a marked fluid volume of an agarose-based filler; and instructions for removing an undesired injection of the filler comprising dispersing the filler with an injection consisting of saline.

In some embodiments, the instructions for removing an undesired injection of the filler further comprises an instruction to fill at least one syringe with saline prior to injection of the agarose-based filler.

In another aspect, the kit for performing a dermal filling procedure comprises a filler container containing a marked fluid volume of an agarose-based filler; and a filler-dispersion container containing a marked fluid volume of saline; wherein the filler container and filler-dispersion container are each connectable to an injection needle and the marked fluid volume of the filler-dispersion container is within a ratio of 1:2 to 2:1 with the marked fluid volume of the filler container.

In some embodiments, the fluid volume of the filler container is between about 0.7 mL and about 3 mL.

In some embodiments, the kit further comprises a second filler-dispersion container containing a marked fluid volume of saline, the second filler-dispersion container being equivalent to the filler-dispersion container.

In one or more embodiments of any of the above aspects, the agarose-based filler is a biocompatible gel including between about 1% and 4% agarose. In one embodiment, the agarose-based filler includes between about 1% and 2% agarose.

In some embodiments, the agarose-based filler is free of hyaluronic acid and derivatives thereof. In one or more embodiments of any of the above aspects, the agarose-based filler further includes between 0.1% and 0.6% hyaluronic acid. In some embodiments, the agarose-based filler includes between about 2% and 4% agarose and 0.3% and 0.6% hyaluronic acid. Specifically, the agarose-based filler can include about 3.5% agarose and about 0.4% hyaluronic acid.

In one or more embodiments, the kit for performing a dermal filling procedure further comprises a heater that controls heating of the filler-dispersion container to substantially human body-temperature. In on embodiment, the kit further comprises further a set of instructions to heat the saline within the filler-dispersion container to substantially human body temperature.

In one or more embodiments of any of the above aspects, the kit further comprises a set of instructions to visually and physically inspect a patient to identify a lump or an undesired pocket of injected agarose-base filler between 1 minutes and 15 days after injection of the filler container. In one embodiment of any of the above aspects, the set of instructions comprises visually and physically inspect a patient to identify a lump or an undesired pocket of injected agarose-base filler between 1 minutes and 30 minutes after injection of the filler container.

In one or more embodiments, the kit for performing a dermal filling procedure further comprises instructions to inject the filler-dispersion container at the location of the lump or the undesired pocket of injected agarose-based filler and to massage the location to disperse the lump or the undesired pocket of injected agarose-based filler.

In one or more embodiments of any of the above aspects the filler container and the filler-dispersion container have substantially the same marked fluid volume.

In one or more embodiments of any of the above aspects, the kit for performing a dermal filling procedure further comprises three or more filler-dispersion containers, each containing a marked fluid volume of saline.

In another aspect of the present technology, provided herein is a method of dispersing an injected agarose-based filler from a patient. The method comprises identifying a lump or an undesired pocket of injected agarose-based filler under the patient's skin; injecting a first container of saline in an amount between about 0.7 mL to about 5 mL into the patient at the location of the lump or undesired pocket of injected agarose-base filler; and massaging the location after injection to disperse the lump or undesired pocket of injected agarose-base filler.

In yet another aspect, the present disclosure relates to a method of dispersing an injected agarose-based filler from a patient, wherein a lump or an undesired pocket of agarose-based filler is present under the patient's skin. The method comprises injecting a first container of saline in an amount between about 0.7 mL to about 5 mL into the patient at the location of the lump or undesired pocket of injected agarose-based filler.

Embodiments of the above aspects can include one or more of the following features. In some embodiments, the method of dispersing an injected agarose-based filler from a patient further comprises heating the saline to approximate body temperature prior to injection. In some embodiments, the method further comprises injecting a second container of saline in an amount between about 0.7 to about 5 mL into the patient at the location of the lump or undesired pocket of injected agarose-base filler. In one or more embodiments, a first massaging step occurs after the injection of the first container of saline and a second massaging step occurs after injecting the second container of saline. In some embodiments, the method further comprises injecting a third container of saline in an amount between about 0.7 to about 5 mL into the patient at the location of the lump or undesired pocket of injected agarose-base filler.

In some embodiments, the injected agarose-based filler was injected into the patients 15 days or less prior to the identifying step.

In some embodiments, the fluid volume of saline contained in the first container is substantially equal to a fluid volume of injected agarose-based filler (about 1:1 ratio of volume of saline to volume of injected agarose-based filler). In other embodiments, the fluid volume of saline contained in the first vial is half of a fluid volume of injected agarose-based filler (1:2 ratio of volume of saline to volume of injected agarose-based filler). In one embodiment, the fluid volume of saline contained in the first container is twice a fluid volume of injected agarose-based filler (2:1 ratio of volume of saline to volume of injected agarose-based filler).

Compared to other HA based injectables, novel agarose-based dermal fillers exhibit good tolerability, excellent persistence, negligible immunological reaction, biocompatibility and maximal safety-all properties combined with immediate volume restoration and predictable outcomes. In addition, HA based fillers tend to increase risk of swelling compared to agarose based dermal fillers. Vascular occlusion is one of the most concerning complication related to swelling properties of HA based fillers. Swelling of HA based fillers due to significant fluid attraction to highly hydrophobic HA can cause the compression of blood vessels. This can lead to a localized occlusion, resulting in skin necrosis, or a distant occlusion causing blindness or cerebral ischemic events (Abduljabbar et al., Journal of Dermatology & Dermatologic Surgery, 2016).

The present disclosure advantageously provides a range of agarose-based dermal fillers that has excellent filler properties, as shall be described in detail herein below. Consistency, controllable size, and concentration-based properties of agaro se-based fillers support modification of agarose-based fillers with different rheological properties. In some embodiments, rheological properties of agarose-based fillers can be customized/tailored to target certain indications and/or certain part of the tissue.

Effective and results-oriented kits and methods are needed for increasing desirable cosmetic outcomes for dermal fillers. Patients demand enhanced physical results through procedures that are both safe and reversible, if need be. The present disclosure provides patients not only with a reversible procedure that can disperse unwanted visual and tactile results up to 15 days after the filler injection, but also uses safe, patient-friendly materials, such as an agarose-based (e.g., a polysaccharide that can be harvested from seaweed) filler and an "eraser" or a filler-dispersion fluid formed of saline.

BRIEF DESCRIPTION OF THE DRAWINGS

The present disclosure will be more fully understood from the following detailed description taken in conjunction with the accompanying drawings, in which.

DETAILED DESCRIPTION

The present technology provides ways to increase safety of dermal filler procedures.

The present disclosure relates to kits and methods for correcting or modifying patient results during or after an agarose-based dermal filler procedure. In particular, the present disclosure is directed to removing mis-positioned dermal filler (such as lumps or undesired pockets of injected agarose-based filler) from a patient using human injectable grade saline.

In general, the present technology relates to methods and kits for dispersing or correcting an agarose-based dermal filler from a patient. When injecting a filler under a patient's skin, errors can occur. Using the methods and kits of the present technology, healthcare professionals can address those errors during the injection procedure and for a 15-day period of time after the injection procedure (e.g., 30 seconds after completion of injection; 1 minutes after injection after completion of injection; 15 minutes after completion of injection; 1 day after completion of injection; 5 days after completion of injection; 1 week after completion of injection; 2 weeks after completion of injection). The methods and kits of the present technology utilize safe and common/known to patient materials (e.g., agarose filler and saline). The methods and kits of the present technology can be used to disperse, correct, or adjust the undesired placement of the agarose-based filler. In some embodiments, the methods and kits of the present technology can be used to disperse pockets of filler, including pockets of filler that may result in adverse compressive pressure being applied to the patient's vascular. As a result, the methods and kits of the present technology provide additional safety advantages over other injectables, as the agarose-based dermal fillers can be dispersed quickly to prevent injury to a patient.

Figure 1A:
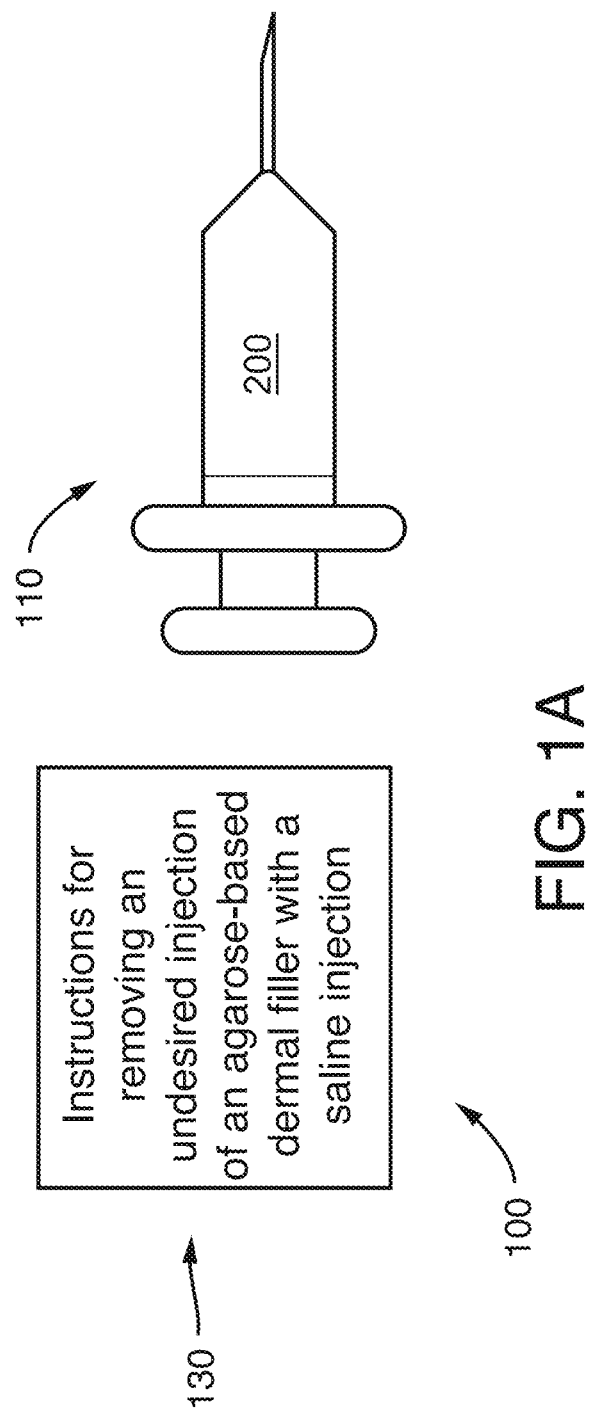
FIGS. 1A and 1B illustrates a kit for performing a dermal filling procedure in accordance with various embodiments described herein.

FIG. 1A illustrates a kit 100 for performing a dermal filling procedure according to various embodiments described herein. In particular, the kit 100 includes a filler container 200 containing a marked fluid volume 110 of an agarose-based filler (e.g. a syringe filled with a marked volume 110 of agarose-based filler, a vial filled with a marked volume 110 of agarose-based filler); and instructions 130 for removing an undesired injection of the filler comprising dispersing the filler with an injection consisting of saline. In some embodiments, the instructions 130 further recommend pre-filling at least one syringe with saline prior to commencing any procedure using the agarose-based fillers. In some embodiments, the instructions for pre-filling syringes with saline further comprise instructions for heating the pre-filled syringes to substantially human body-temperature prior to commencing any procedure using the agarose-based filler. In one embodiment, the instructions for pre-filling syringes with saline further comprise instructions for heating the saline to substantially human body-temperature prior to filling the syringes.

In some embodiments, a filler container 200 is able to connect to luer-lock connector.

Figure 1B:
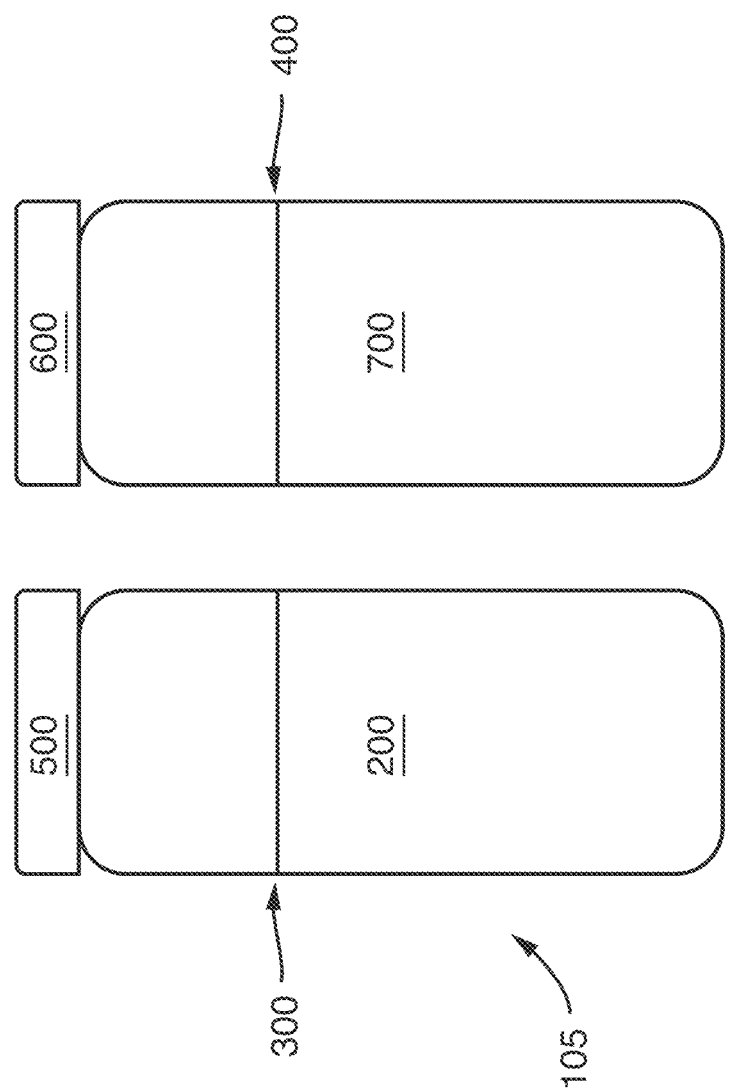

FIG. 1B illustrates a kit 105 for performing a dermal filling procedure according to various embodiments described herein. In particular, the kit 105 includes a filler container 200 containing a marked fluid volume 300 of an agarose-based filler and a filler-dispersion container 700 containing a marked fluid volume 400 of saline; wherein the filler container and filler-dispersion container are each connectable to an injection needle and the marked fluid volume of the filler-dispersion container is within a ratio of 1:2 to 2:1 with the marked fluid volume of the filler container.

The filler container 200 and the filler-dispersion container 700 can include syringes, carpule, ampoule, tubes, vials, bags, bottles, or other pre-formed containers.

The container can be made of a variety of materials including plastic or glass materials.

The filler container 200 and the filler-dispersion container 700 are each connectable to an injection needle through 500 and 600, respectively. 500 and 600 can be made of a variety of materials and variety of shapes that allows connection to a needle.

In some embodiment, 500 and 600 are able to connect to luer-lock connector.

In some embodiments, 500 and 600 can include a lid having elastic materials that allows a needle pass through the lid.

The present technology is also directed to injectable agarose-based dermal filler compositions that have advanced rheological properties while at the same time have low extrusion forces. These agarose-based dermal fillers offer good longevity, are easily injectable and have improved rheological properties (i.e., G Prime (G') and dynamic viscosity) resulting in an excellent ability to create volume. The present disclosure further relates to use of such agarose-based dermal filler compositions for cosmetic and therapeutic purposes.

In some embodiments, the agarose-based gel dermal filler has been customized/modified to provide the advanced rheological properties.

Present disclosure is further directed to kits that include novel range of agarose-based dermal fillers that have tunable/customizable rheological properties. The kits can also include instructions as to how the most appropriate agarose-based filler is selected for administration into a different target tissue of a subject.

By a controlled purification process, the agarose-based gel dermal fillers of the present technology can achieve the desired rheological profile, thereby allowing the dermal filler to achieve better results over commercially available products—such as those including HA.

Furthermore, the present filler composition exhibits slow absorption and offers excellent results in terms of softness and elasticity when utilized in cosmetic surgery involving the face.

As used herein, the term "about" means that the numerical value is approximate and small variations would not significantly affect the practice of the disclosed embodiments. Where a numerical limitation is used, unless indicated otherwise by context, "about" means the numerical value can vary by ±10% and remain within the scope of the disclosed embodiments.

Unless specified otherwise, "percentage (%) by weight" refers to the weight of the single component with respect to the total weight of the composition.

As used herein, "cosmetic" is an adjective referring to improving the appearance of a surface or covering defects. Typically, cosmetic compositions can be used to improve aesthetic rather than functional aspects of a surface. Most commonly, cosmetic compositions are formulated for application as a health and beauty treatment or for affecting personal appearance of the body, for example, keratinous surfaces such as skin, hair, nails, and the like.

As used herein, "formulation" and "composition" may be used interchangeably and refer to a combination of elements that is presented together for a given purpose. Such terms are well known to those of ordinary skill in the art.

As used herein, the term "container", is meant to include syringes, carpule, ampoule, tubes, vials, bags, bottles, or other pre-formed containers or other means useful for housing a product of interest, e.g. dermal filler composition. Containers may be fabricated using standard methods or may be containers as available and provided from known manufactures or suppliers. They may be manufactured from transparent, semi-transparent or opaque plastic materials, glass, metal or other suitable materials.

As used herein, the term "dermal filler" broadly refers to a material or composition designed to add volume to areas of soft tissue deficiency. This is, the term "dermal filler" should not be construed as imposing any limitations as to the location and type of injection, and it generally encompasses uses at multiple levels beneath the dermis, for example sub-muscularly above the periosteum and in the subcutaneous plane. Within the meaning of the present invention, the term "soft tissue" generally relates to tissues that connect, support, or surround other structures and organs of the body. In the present invention, soft tissues include, for example, muscles, tendons (bands of fiber that connect muscles to bones), fibrous tissues, fat, blood vessels, nerves, and synovial tissues (tissues around joints).

According to the present disclosure, the injectable dermal filler composition is a gel. The term "gel", as used herein, generally refers to a material having fluidity at room temperature between that of a liquid and solid. In addition, the term "gel" is intended to mean a material capable of absorbing water (i.e. a "hydrogel"). Within the present disclosure, the injectable dermal filler composition generally comprises a physiologically acceptable carrier fluid, such as an apyrogenic isotonic buffer, in particular a physiological saline solution that is preferably buffered.

As used herein, the term "hyaluronic acid" or "HA", means hyaluronic acid, hyaluronate, and any hyaluronate salt such as sodium hyaluronate.

Furthermore, the dermal filler composition of the present disclosure is "injectable". This means that the dermal filler composition is suitable for injection into the skin or other tissue in order to bring the dermal filler composition to the desired target site. An "injectable" composition within the meaning of the present invention can be dispensed from syringes under normal conditions under normal pressure.

The term "saline" or "saline solution" refers to a solution of salt (e.g. NaCl) in water.

As used herein, the term "subject" in the sense of the present invention is any individual or patient, usually a human, in need of the treatment of a particular condition or disease.

Hyaluronic Acid (HA)

In some embodiments, the hyaluronic acid is present in the filler composition as such and/or in the form of a pharmaceutically acceptable salt, intended as a salt that is suitable for in-vivo administration. In this regard, the preferred pharmaceutically acceptable salts of hyaluronic acid consist of alkali metal salts, sodium hyaluronate (CAS No. 9067-32-7) being particularly preferred.

The hyaluronic acid (CAS No. 9004-61-9) is an unbranched glycosaminoglycan, obtained by condensation of thousands of disaccharide units made up of residues of glucuronic acid and N-acetylglucosamine.

In any case, the hyaluronic component (acid or salt) is present in amounts that can vary between 0.1 and 0.6% by weight.

Agarose

Chemically, agarose is a polysaccharide polymer, generally extracted from red algae or seaweed. Agarose is a linear polymer made up of repeating units of agarobiose, a disaccharide made up of D-galactose and 3,6-anhydro-L-galactopyranose. Agarose is one of the two principal components of agar, and is purified from agar by removing agar's other component, agaropectin. Agarose is the component responsible for the high-strength gelling properties of agar and the agaropectin provides the viscous properties.

Agarose is available as a white powder which dissolves in near-boiling water, and forms gel when it is cooled. Agarose also can have high gel strength at low concentration, thus providing gel networks with high water content. The natural agarose polymer contains charged groups, such as pyruvate and sulphate. The agarose polysaccharide also contains uncharged methyl groups. The extent of natural methylation is directly proportional to the gelling temperature. Unexpectedly, synthetically methylated agaroses have lower, rather than higher, gelling temperatures, and the degree of synthetic methylation is inversely proportional to the melting temperature.

Advantageously, due to its particular concentration of agarose, the present filler composition makes it possible to achieve slow absorption by the human body, which translates into a prolonged permanence time of the filler in the injection site, enabling a reduction or even the elimination of subsequent refilling treatments.

In some embodiments, the agarose and the hyaluronic acid component tend to form an intersecting structure, in which they intersect one with the other, which characterizes the invention and provides remarkable properties in terms of viscosity and injectability. Moreover, in-vivo, the hyaluronic acid is quickly absorbed by the organism and said intersecting structure with the agarose remains. While not wishing to be bound by any particular theory, the remaining (agarose) structure thus takes on a physical form that exhibits channels or tunnels (previously occupied by the hyaluronic acid) and differs from the form that the agarose would have if injected alone, without the combination with hyaluronic acid. These channels provide the injected filler with increased elasticity, a high degree of softness and a high level of bioavailability, which are not otherwise achievable by injecting agarose alone at the concentrations indicated.

Furthermore, the present filler composition exhibits slow absorption and offers excellent results in terms of softness and elasticity also when utilized in cosmetic surgery involving the face, or particularly sensitive areas.

In one embodiment, the composition comprises agarose in amounts comprised between 0.1 and 6% by weight, even more preferably between 0.5 and 4% by weight.

Different types of agarose can be used in various embodiments of the present invention. In different embodiments agarose has a molecular weight of about 10,000 to 1,500,000 daltons.

The agarose used in the disclosed kits, methods and compositions may be commercially obtained or prepared by a user. The disclosed agarose may, in some embodiments, include one or more crude, purified, derivatized or modified agars or agaroses. For example, in certain embodiments, the agarose is selected from natural agarose, purified agarose, modified agarose, and derivatized agarose. The agarose may also be used as mixtures with other compatible polymers and additives such as agar, carrageenan, chitosan, alginate, gelatin, hyaluronic acid, collagen, in some embodiments. In certain embodiments, the agarose is Gracilaria-derived agarose. Gracilaria-derived agarose has a higher methoxy content than agarose derived from other sources (e.g, Gelidium). Agaroses from other seaweeds, for example, Pterocladia or Gelidiella may also be used as the disclosed agarose.

Furthermore, some other embodiments of the present invention utilize substituted agarose with low melting temperature, where substituents can be selected from the group consisting of hydroxyethyl, hydroxypropyl, methyl, allyl and acetyl substituents. For example, in one of the embodiments agarose melting temperature is 90° C. and the agarose solution is heated up to 100° C. in order to achieve complete dissolving of agarose.

Commonly the natural polymer is modified in order to obtain agarose with different melting and gelling temperatures. Usually, the sulphate and pyruvate groups are reduced in order to obtain uncharged polymer. Furthermore, the charged groups can be substituted with hydroxy ethyl or vinyl (allyl) groups to the various extents in order to obtain agarose with low melting temperature.

Those skilled in the art will recognize, or be able to ascertain using no more than routine experimentation, numerous equivalents to the specific procedures described herein. Such equivalents were considered to be within the scope of this technology and are covered by the following claims. The contents or all references, issued patents, and published patent applications cited throughout this application are hereby incorporated by reference.

Further Ingredients

The compositions disclosed herein can include additional cosmetic agents that supplement and improve the appearance of skin. The cosmetic active ingredients may include, but are not limited to, antioxidants, vitamins, tension agents, and moisturizers.

The compositions disclosed herein can further include additional ingredients (agents). Examples of which can be included in the present dermal filler formulations are anti-itch, anti-cellulite, anti-scarring, and anti-inflammatory agents, anesthetics, anti-irritants, vasoconstrictors, vasodilators, as well as agents to prevent/stop bleeding, and improve/remove pigmentation, moisturizers, desquamating agents, tensioning agents, anti-acne agents.

Anti-itch agents can include methyl sulphonyl methane, sodium bicarbonate, calamine, allantoin, kaolin, peppermint, tea tree oil, camphor, menthol, hydrocortisone and combinations thereof.

Anti-cellulite agents can include forskolin, xanthine compounds such as, but not limited to, caffeine, theophylline, theobromine, and aminophylline, and combinations thereof.

Anesthetic agents can include lidocaine, benzocaine, butamben, dibucaine, oxybuprocaine, pramoxine, proparacaine, proxymetacaine, tetracaine, and combinations thereof.

Antiscarring agents can include IFN-.gamma., fluorouracil, poly (lactic-co-glycolic acid), methylated polyethylene glycol, polylactic acid, polyethylene glycol and combinations thereof.

Anti-inflammatory agents can include dexamethasone, prednisolone, corticosterone, budesonide, estrogen, sulfasalazine, mesalamine, cetirizine, diphenhydramine, antipyrine, methyl salicylate, loratadine, and derivatives and combinations thereof.

In fact, in particular, in addition to the components described above and characterizing the invention, the present composition can contain additional compounds, for example to further improve bioavailability and/or to increase in vivo stability over time. In this regard, the composition can also comprise at least one protein and/or at least one natural amino acid.

The filler composition preferably comprises at least one protein or one amino acid in amounts that can vary from 0.01% to 0.6% by weight, values comprised between 0.02 and 0.15% being particularly preferred.

In one embodiment, the filler composition of the invention comprises the protein resilin, preferably in amounts comprised between 0.01 and 0.1% by weight, even more preferably comprised between 0.01 and 0.04%. The presence of this protein makes it possible to increase the sensitivity of the tissues adjacent to the injection site, ensuring greater in-vivo stability and thus longer duration of the cosmetic and/or therapeutic results achieved.

Aspects of the present specification provide, in part, a fluid composition that can optionally comprise or not comprise an anesthetic agent. An anesthetic agent is preferably a local anesthetic agent, i.e., an anesthetic agent that causes a reversible local anesthesia and a loss of nociception, such as, e.g., aminoamide local anesthetics and aminoester local anesthetics. The amount of an anesthetic agent included in a fluid composition disclosed in the present specification is an amount effective to mitigate pain experienced by an individual upon administration of the composition. As such, the amount of an anesthetic agent included in a fluid composition disclosed in the present specification is between about 0.1% to about 5% by weight of the total composition. Non-limiting examples of anesthetic agents include lidocaine, ambucaine, amolanone, amylocalne, benoxinate, benzocaine, betox-ycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phen-acaine, phenol, piperocaine, piridocaine, polidocanol, pramoxine, prilocaine, procaine, propanocaine, propara-caine, propipocaine, propoxycaine, pseudococaine, pyr-rocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, and trimecaine. A non-limiting example of a combination local anesthetic is lidocaine/prilocaine (EMLA).

In an equally preferred embodiment, the composition can contain, in addition to or in place of the protein, at least one natural amino acid. The presence of at least one amino acid compound is useful particularly for increasing the biocompatibility of the injected composition, while also making it possible to reduce undesirable phenomena related to the migration of the filler injected.

Rheological Properties

Aspects of the present specification provide, in part, a dermal filler compositions disclosed in the present specification exhibiting a complex modulus, an elastic modulus, a viscous modulus and a tan δ. Compositions disclosed in the present specification are viscoelastic in that the composition has an elastic component (solid-like) and a viscous component (liquid-like) when a force is applied (stress, deformation). The rheological attribute that described this property is the complex modulus (G*), which defines a compositions total resistance to deformation. The complex modulus can be defined as the sum of the elastic modulus (G') and the viscous modulus (G"). Falcone, et al., Temporary Polysaccharide Dermal Fillers: A Model for Persistence Based on Physical Properties, Dermatol Surg. 35(8): 1238-1243 (2009); Tezel, supra, 2008; Kablik, supra, 2009; Beasley, supra, 2009; each of which is hereby incorporated by reference in its entirety.

Elastic modulus characterizes the firmness of a composition and is also known as the storage modulus because it describes the storage of energy from the motion of the composition. The elastic modulus describes the interaction between elasticity and strength (G'=stress/strain) and, as such, provides a quantitative measurement of a composition's hardness or softness. Although depending on the speed at which the force is applied, a stiffer composition will have a higher elastic modulus and it will take a greater force to deform the material a given distance, such as, e.g., an injection.

Viscous modulus is also known as the loss modulus because it describes the energy that is lost as viscous dissipation. Tan δ is the ratio of the viscous modulus and the elastic modulus, tan δ=G'/G". Falcone, supra, 2009. A lower tan δ corresponds to a stiffer, harder, or more elastic composition.

Thus, in an embodiment, a fluid composition exhibits a complex modulus. In aspects of this embodiment, a fluid composition exhibits a complex modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, or about 800 Pa. In other aspects of this embodiment, a fluid composition exhibits a complex modulus of, e.g., at most 25 Pa, at most 50 Pa, at most 75 Pa, at most 100 Pa, at most 125 Pa, almost 150 Pa, at most 175 Pa, almost 200 Pa, almost 250 Pa, almost 300 Pa, almost 350 Pa, almost 400 Pa, almost 450 Pa, almost 500 Pa, almost 550 Pa, almost 600 Pa, at most 650 Pa, at most 700 Pa, at most 750 Pa, or at most 800 Pa. In yet other aspects of this embodiment, a fluid composition exhibits a complex modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, or about 125 Pa to about 800 Pa.

In another embodiment, a fluid composition exhibits an elastic modulus. In aspects of this embodiment, a fluid composition exhibits an elastic modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, or about 800 Pa. In other aspects of this embodiment, a fluid composition exhibits an elastic modulus of, e.g., at most 25 Pa, at most 50 Pa, at most 75 Pa, at most 100 Pa, at most 125 Pa, almost 150 Pa, at most 175 Pa, almost 200 Pa, almost 250 Pa, almost 300 Pa, almost 350 Pa, almost 400 Pa, almost 450 Pa, almost 500 Pa, almost 550 Pa, almost 600 Pa, at most 650 Pa, at most 700 Pa, at most 750 Pa, or at most 800 Pa. In yet other aspects of this embodiment, a fluid composition exhibits an elastic modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, or about 125 Pa to about 800 Pa.

In another embodiment, a fluid composition exhibits a viscous modulus. In aspects of this embodiment, a fluid composition exhibits a viscous modulus of, e.g., about 10 Pa, about 20 Pa, about 30 Pa, about 40 Pa, about 50 Pa, about 60 Pa, about 70 Pa, about 80 Pa, about 90 Pa, about 100 Pa, about 110 Pa, about 120 Pa, about 130 Pa, about 140 Pa, or about 150 Pa. In other aspects of this embodiment, a fluid composition exhibits a viscous modulus of, e.g., at most 10 Pa, at most 20 Pa, at most 30 Pa, at most 40 Pa, at most 50 Pa, at most 60 Pa, at most 70 Pa, at most 80 Pa, at most 90 Pa, at most 100 Pa, almost 110 Pa, almost 120 Pa, almost 130 Pa, almost 140 Pa, or at most 150 Pa. In yet other aspects of this embodiment, a fluid composition exhibits a viscous modulus of, e.g., about 10 Pa to about 30 Pa, about 10 Pa to about 50 Pa, about 10 Pa to about 100 Pa, about 10 Pa to about 150 Pa, or about 70 Pa to about 100 Pa.

In another embodiment, a fluid composition disclosed in the present specification exhibiting a tan δ. In aspects of this embodiment, a fluid composition exhibits a tan δ of, e.g., about 0.1, about 0.2, about 0.3, about 0.4, about 0.5, about 0.6, about 0.7, about 0.8, about 0.9, or about 1.0. In other aspects of this embodiment, a fluid composition exhibits a tan δ of, e.g., almost 0.1, almost 0.2, almost 0.3, at most 0.4, almost 0.5, at most 0.6, at most 0.7, at most 0.8, almost 0.9, or at most 1.0. In yet other aspects of this embodiment, a fluid composition exhibits a tan δ of, e.g., about 0.1 to about 0.3, about 0.3 to about 0.5, about 0.3 to about 0.6, about 0.1 to about 0.5, or about 0.1 to about 0.6.

Aspects of the present specification provide, in part, a fluid composition disclosed in the present specification exhibiting a dynamic viscosity. Viscosity is resistance of a fluid to shear or flow caused by either shear stress or tensile stress. Viscosity describes a fluid's internal resistance to flow caused by inter-molecular friction exerted when layers of fluids attempt to slide by one another and may be thought of as a measure of fluid friction. The less viscous the fluid, the greater its ease of movement (fluidity).

Viscosity can be defined in two ways; dynamic viscosity (μ, although η is sometimes used) or kinematic viscosity (v). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s). Dynamic viscosity can be expressed as τ=μdvx/dz, where τ shearing stress, μ dynamic viscosity, and dvx/dz is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity (v) is the ratio of dynamic viscosity to density, a quantity in which no force is involved and is defined as follows: v=μ/ρ, where μ is the dynamic viscosity ρ is density with the SI unit of kg/m³. Kinematic viscosity is usually measured by a glass capillary viscometer as has an SI unit of m²/s.

The viscosity of a fluid is highly temperature dependent and for either dynamic or kinematic viscosity to be meaningful, the reference temperature must be quoted.

Thus, in an embodiment, a fluid composition comprising a matrix polymer and a stabilizing component exhibits a dynamic viscosity. In aspects of this embodiment, a fluid composition comprising a matrix polymer and a stabilizing component exhibits a dynamic viscosity of, e.g., about 10 Pa·s, about 20 Pa·s, about 30 Pa·s, about 40 Pa·s, about 50 Pa·s, about 60 Pa·s, about 70 Pa·s, about 80 Pa·s, about 90 Pa·s, about 100 Pa·s, about 125 Pa·s, about 150 Pa·s, about 175 Pa·s, about 200 Pa·s, about 225 Pa·s, about 250 Pa·s, about 275 Pa·s, about 300 Pa·s, about 400 Pa·s, about 500 Pa·s, about 600 Pa·s, about 700 Pa·s, about 750 Pa·s, about 800 Pa·s, about 900 Pa·s, about 1,000 Pa·s, about 1,100 Pa·s, or about 1,200 Pa·s. In other aspects of this embodiment, a fluid composition comprising a matrix polymer and a stabilizing component exhibits a dynamic viscosity of, e.g., at most 10 Pa·s, at most 20 Pa·s, almost 30 Pa·s, almost 40 Pa·s, at most 50 Pa·s, at most 60 Pa·s, at most 70 Pa·s, at most 80 Pa·s, at most 90 Pa·s, at most 100 Pa·s, at most 125 Pa·s, at most 150 Pa·s, almost 175 Pa·s, almost 200 Pa·s, almost 225 Pa·s, at most 250 Pa·s, at most 275 Pa·s, at most 300 Pa·s, at most 400 Pa·s, almost 500 Pa·s, almost 600 Pa·s, almost 700 Pa·s, at most 750 Pa·s, at most 800 Pa·s, at most 900 Pa·s, or at most 1000 Pa·s. In yet other aspects of this embodiment, a fluid composition comprising a matrix polymer and a stabilizing component exhibits a dynamic viscosity of, e.g., about 10 Pa·s to about 100 Pa·s, about 10 Pa·s to about 150 Pa·s, about 10 Pa·s to about 250 Pa·s, about 50 Pa·s to about 100 Pa·s, about 50 Pa·s to about 150 Pa·s, about 50 Pa·s to about 250 Pa·s, about 100 Pa·s to about 500 Pa·s, about 100 Pa·s to about 750 Pa·s, about 100 Pa·s to about 1,000 Pa·s, about 100 Pa·s to about 1,200 Pa·s, about 300 Pa·s to about 500 Pa·s, about 300 Pa·s to about 750 Pa·s, about 300 Pa·s to about 1,000 Pa·s, or about 300 Pa·s to about 1,200 Pa·s.

Methods of Administration and Methods of Use

The dermal filler composition of the present invention is generally administered in an effective amount to a subject by injection, such as by subcutaneous or intradermal injection. For example, the composition may be intradermally or subcutaneously injected using the serial puncture technique. The term "effective amount" refers to the amount of the (injectable) soft tissue filler composition sufficient to effect beneficial or desired cosmetic (aesthetic) or therapeutic results.

As used herein, the term "injectable" refers to a composition disclosed in the present specification having the properties necessary to administer the composition into a dermal region of an individual using an injection device with a fine needle. As used herein, the term "fine needle" refers to a needle that is 27 gauge or smaller.

In one aspect provided herein is an injectable biomaterial comprising agarose-based dermal fillers, wherein the biomaterial is formulated for dermal or subdermal administration into a target tissue of a subject. In one aspect provided here is a composition comprising the agarose-based dermal fillers, wherein the formulation is suitable for dermal injection via a needle no larger than 16-gauge, 18-gauge, 20-gauge, 22-gauge, 24-gauge, 26-gauge, 27-gauge, 28-gauge, 29-gauge, 30-gauge, 31-gauge, or smaller than 31-gauge.

Aspects of the present specification provide, in part, a method having a step of sterilizing the dermal fillers composition disclosed in the present specification. As used herein, the term "sterilizing" refers to any method known in the art to effectively kill or eliminate transmissible agents without substantially altering of degrading a fluid composition disclosed in the specification. A sterilized composition can remain stable for about 3 months to about 3 years.

One method of sterilization of the dermal filler composition disclosed herein is by autoclave. Autoclaving can be accomplished by applying a mixture of heat, pressure and moisture to a sample in need of sterilization. Many different sterilization temperatures, pressures and cycle times can be used for this step. For example, the filled syringes may be sterilized at a temperature of at least about 120° C. to about 130° C. or greater. Moisture may or may not be utilized. The pressure applied is in some embodiments depending on the temperature used in the sterilization process. The sterilization cycle may be at least about 1 minute to about 20 minutes or more.

Another method of sterilization incorporates the use of a gaseous species which is known to kill or eliminate transmissible agents. Preferably, ethylene oxide is used as the sterilization gas and is known in the art to be useful in sterilizing medical devices and products.

A further method of sterilization incorporates the use of an irradiation source which is known in the art to kill or eliminate transmissible agents.

In some embodiments, a syringe is filled with a dermal filler composition disclosed in the present specification. In aspects of this embodiment, a syringe filled with the composition is sterilized by autoclaving, gas sterilization, or irradiation. In other aspects of this embodiment, a syringe filled with a fluid composition can remain stable after sterilization for about 3 months, about 6 months, about 9 months, about 12 months, about 18 months, about 24 months, about 30 months, or about 36 months.

The present disclosure relates to use of a dermal filler composition for cosmetic applications, e.g., for improving the visual appearance, in particular of the face. Cosmetic applications include, but are not limited to, augmenting or filling of wrinkles and lines of the skin, in particular of facial lines and facial wrinkles (e.g., glabellar lines, nasolabial folds, chin folds, marionette lines, buccal commissures, peri-oral wrinkles, and crow's feet). Other exemplary cosmetic applications include filling cutaneous depressions, masking scars and temples, providing subdermal support of the brows, malar and buccal fat pads, treating tear troughs, nose, chin and jawline corrections, increasing the volume of the lips, augmenting cheeks, treating the perioral region, infraorbital region and facial asymmetries, and/or improve skin hydration and skin texture.

The present disclosure also relates to a method for replacing or filling of a biological tissue or increasing the volume of the biological tissue for cosmetic purposes, comprising administering to a subject in need thereof an effective amount of the dermal filler composition according to the present invention.

The present disclosure further relates a method of treating a soft tissue condition of an individual by administering a dermal filler composition. As used herein, the term "treating" refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a dermal filler composition disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a composition disclosed herein.

Kits

Kits containing the agarose-based dermal filler compositions are described herein. Part of the kit can be a sterile container (e.g. vial or syringe) containing the filler composition and optionally one or more additives or excipients. The filler composition may be neat (e.g., free of solvent) or the composition may be dissolved or dispersed in a pharmaceutically acceptable solvent or saline. The kit may further contain a sterile container containing the pharmaceutically acceptable solvent or saline for dispersing the agarose-based dermal filler to increase safety of the dermal filling procedures.

In some embodiments, the kit may further contain more than one container including saline (human injectable grade saline) in order to or modify patient results during or after an agarose-based dermal filler procedure. In some embodiments, saline is used for removing lump or undesired pockets of injected agarose-based filler from a patient.

In some embodiments, saline is used for removing lumps or undesired pockets of injected agarose-based filler from a patient. In some embodiments, saline is used to disperse a misplaced injectable to prevent injury or trauma to the patient (e.g., to reduce compressive forces and prevent further injury to vascular).

In one or more embodiments, the kit further comprise instructions to inject the saline at the location of the lump or the undesired pocket of injected agarose-based filler compositions and to massage the location to disperse the lump or the undesired pocket of injected agarose-based filler.

In one aspect, disclosed herein is a kit for performing a dermal filling procedure comprising: a filler vial containing a marked fluid volume of an agarose-based filler; a filler-dispersion vial containing a marked fluid volume of saline; wherein the filler vial and filler-dispersion vial are each connectable to an injection needle and the marked fluid volume of the filler-dispersion vial is within a ratio of 1:2 to 2:1 with the marked fluid volume of the filler vial.

In some embodiments, the kit may contain a device or devices for administering the agarose-based dermal filler composition. In one embodiment, the device would have an outlet for the composition, an ejector for expelling the composition and a hollow tubular member fitted to the outlet for administering the polymer into a subject. For example, the kit may contain a syringe loaded with the composition disclosed herein, wherein the syringe has a fixation point (i.e., a luer lock) for a needle and a set of needles with various gauges suitable for various applications. The kit may also contain instructions for how to administer the dermal filler compositions.

In one or more embodiments, the kit may contain novel range of agarose-based dermal fillers that have tunable/customizable rheological properties and instructions as to how the most appropriate agarose-based filler is selected for administration into a different target tissue of a subject.

In one aspect, the present disclosure relates to a kit comprising at least two injectable dermal filler compositions comprising agarose-based fillers independently selected from: first composition comprising agarose in an amount no more than 5.0% or no smaller than 3.0% by weight and hyaluronic acid or a pharmaceutically acceptable salt thereof in an amount no more than 0.6% or no smaller than 0.1% by weight; second composition comprising agarose in an amount no more than 3.0% or no smaller than 1.0% by weight and hyaluronic acid or a pharmaceutically acceptable salt thereof in an amount no more than 0.6% or no smaller than 0.1% by weight; third composition comprising agarose in an amount no more than 3.0% or no smaller than 1.0% by weight, and optionally instructions for use.

In some embodiments, the first composition is suitable for performing deep volumetric filling, jawline enhancement, chin augmentation, malar zygomatic arch, sub-malar volumization, or non-surgical rhinoplasty.

In one or more embodiments, the first composition may be used as a deep volumizer.

In some embodiments, the second composition is suitable for performing medium to deep volumization of deep wrinkles and/or nasolabial fold, jawline enhancement, chin augmentation, or malar and sub-malar volumization, In some embodiments, the third composition is suitable for performing tear through deformity correction, lips enhancement, lines and lip contouring, wrinkle treatment, lines and lip contouring.

Examples

The examples provided below shows the safety of agarose-based dermal filler compositions according to the present disclosure by evaluating the effectiveness of saline solutions on removing the lump or undesired pocket of injected agarose-base filler. The experiments also demonstrated that agarose-based dermal filler compositions of the present disclosure possess superior mechanical properties (i.e. modulus of elasticity (G') viscosity) comparable to properties of HA-based comparator on the market.

Rheology Measurements

The agarose-based dermal filler (Algeness® DF, 3.5% Agarose and 0.4% HA) used for rheological testing was prepared following the method described in U.S. 2020/0216621 A1 and U.S. 2020/0139347 A1.

Rheological testing was performed on agarose gel filler on a crosslinked HA comparator (Juvederm® Voluma® XC from Allergan Aesthetics) that is CE-marked and US FDA approved for deep (subcutaneous and/or supraperiosteal) injection for cheek augmentation to correct age-related volume deficit. Testing was performed in an independent laboratory, using a parallel plate-to-plate rheometer at fixed ambient temperature and humidity. Oscillatory shear deformation testing comprised shear rate sweeps (0.1 to 100 s-1 range), time sweeps (1 s-1 shear rate) and frequency sweeps in shear. This measured elastic modulus (G') and viscous modulus (G"); how the gels thinned out as applied force was increased (Eta*); and changes in rheological properties after agarose gel was mixed 1:1 by volume with normal (0.9%) saline and HA filler was mixed 1:1 with hyaluronidase. Static compression testing was also performed to provide a measure of each filler's resistance to constant deformation (at a rate of 0.1 mm/s).

Figure 2:
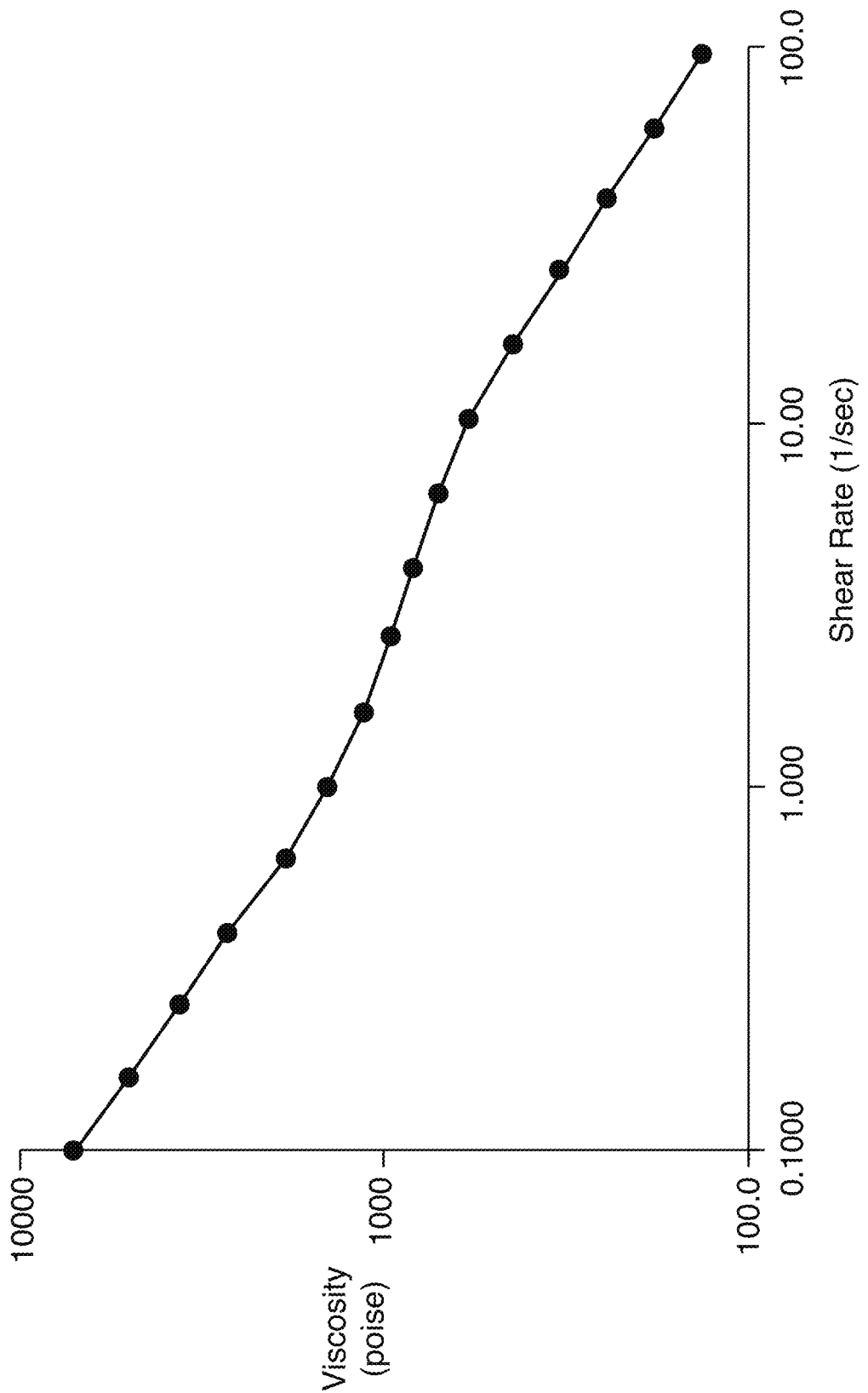
FIG. 2 illustrates viscosity data as a function of shear rate at ambient temperature for a hyaluronic acid based injectable, Voluma® XC, available from Allergan Aesthetics under the trade name Juvederm®. The data indicate shear-thinning behavior and a viscosity that goes from about 7,200 P at 0.1 $s^{-1}$ to 130 P at 100 $s^{-1}$.
Figure 3:
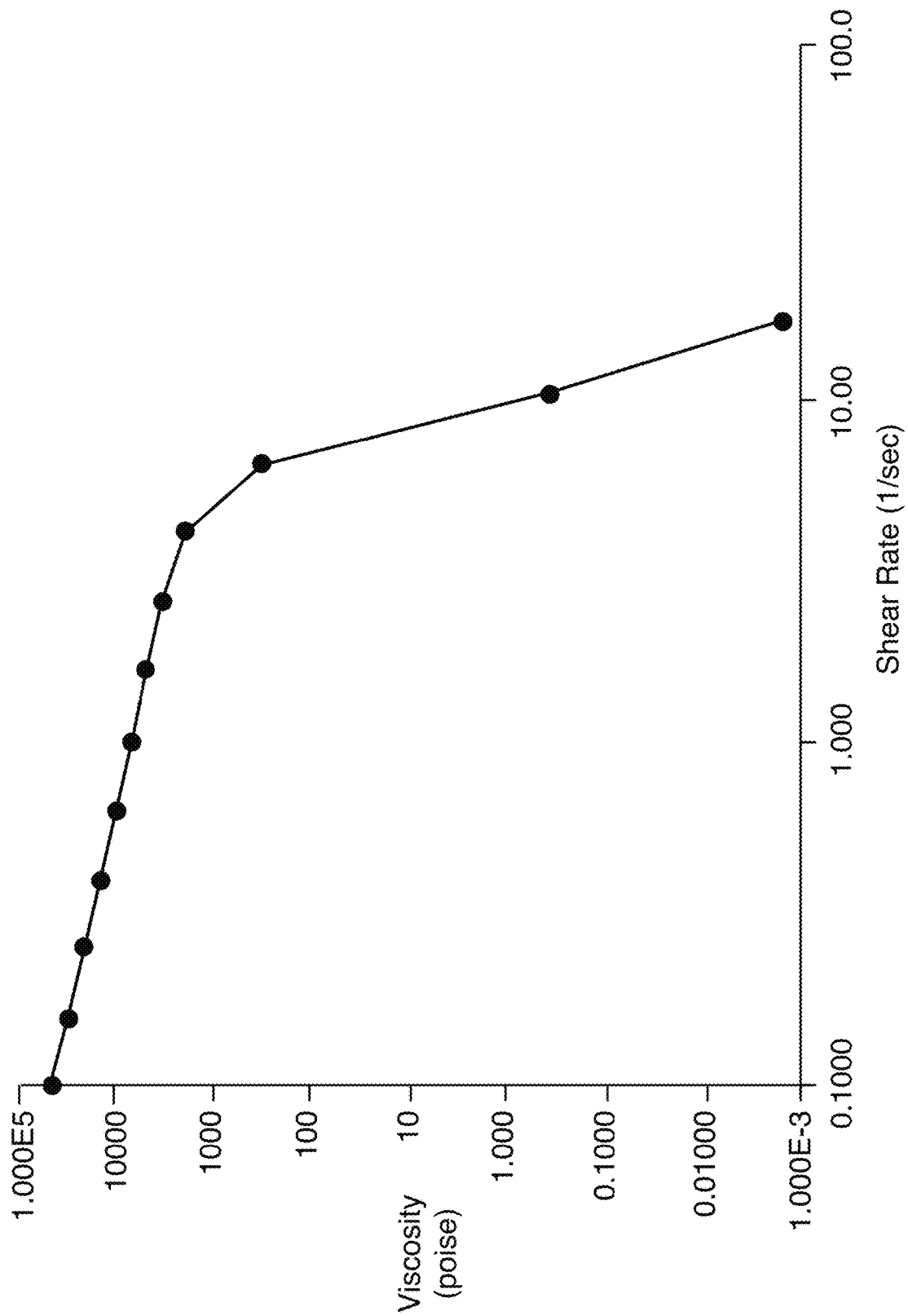
FIG. 3 illustrates viscosity data as a function of shear rate at ambient temperature for Algeness® DF, an agarose based filler, available under the tradename Algeness from Advanced Aesthetic Technologies, Inc. From low to intermediate shear rates, the data indicate shear-thinning behavior. The relatively steep drop in viscosity above 4 $s^{-1}$ is likely due to material that is spun out of from the parallel plates.
Figure 4:
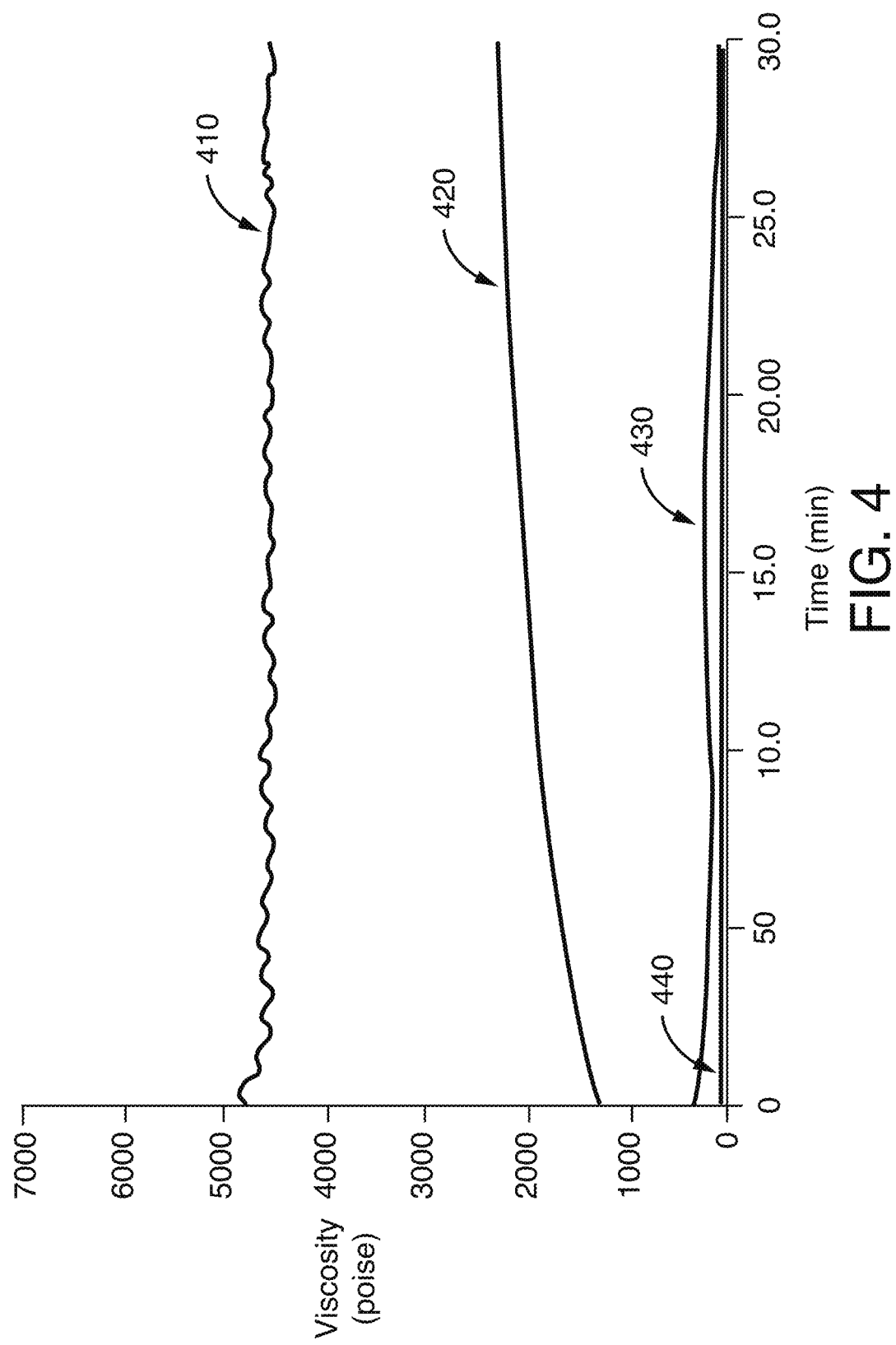
FIG. 4 illustrates overlay of the viscosity versus time data for the Voluma® XC and Algeness® DF samples. From top to bottom, curves belong to Algeness® DF (410), Voluma® XC (420), Voluma® XC+Hyaluronidase (430), and Algeness® DF+saline (440) respectively. For the same level of dilution (i.e., 1:1) the Algeness® DF sample shows a greater reduction in viscosity compared to Voluma® XC.
Figure 5:
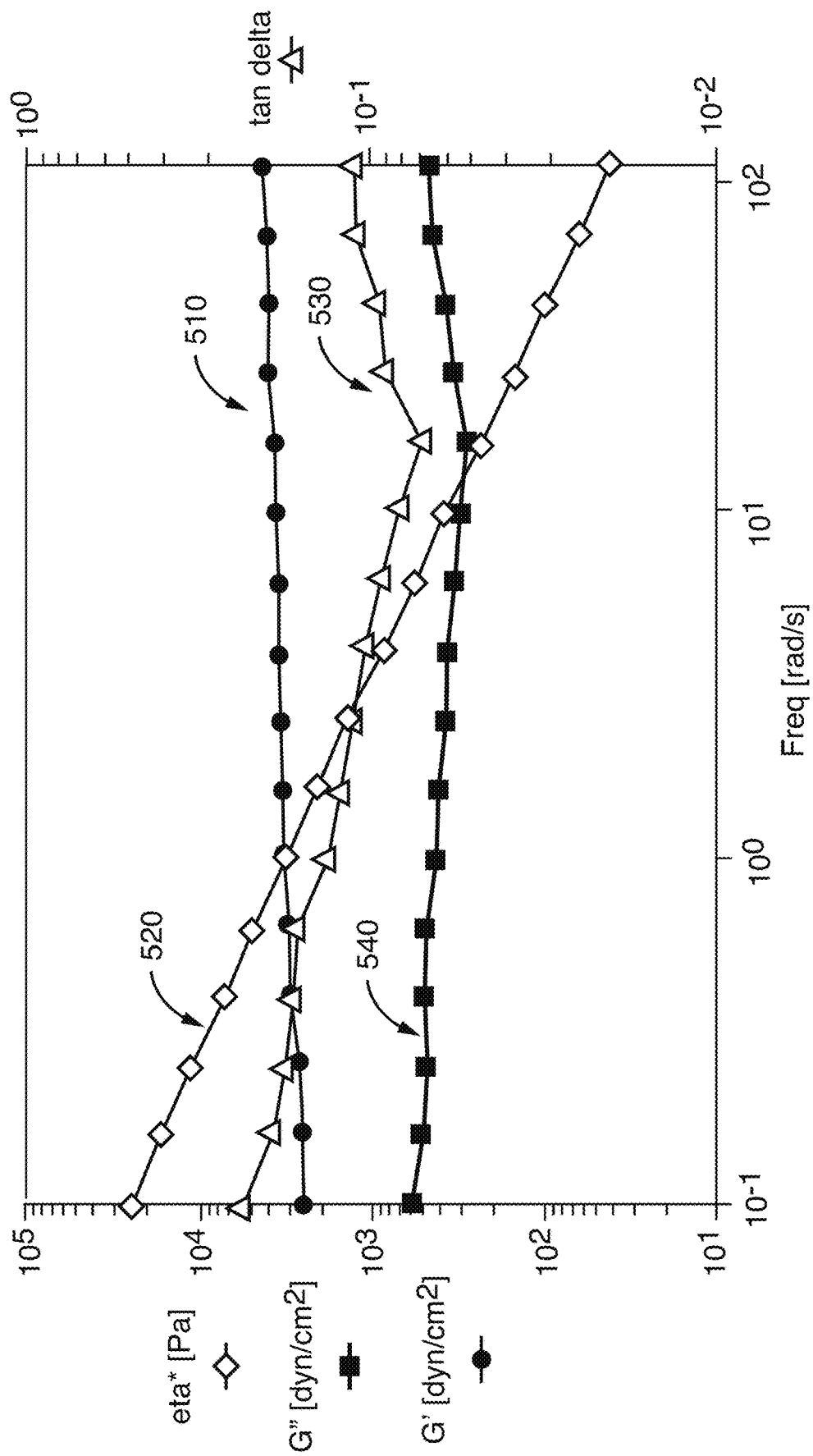
FIG. 5 illustrates shear dynamic mechanical properties as a function of frequency at ambient temperature for Voluma® XC. The complex shear viscosity (Eta*) data (520) indicates shear-thinning behavior. The tan delta data (530) suggest a higher proportion of solid-like (compared to liquid-like) behavior over the frequency range. The tan delta data (530) was obtained using elastic modulus data, G' (510) and loss modulus data, G" (540) presented in the figure.
Figure 6:
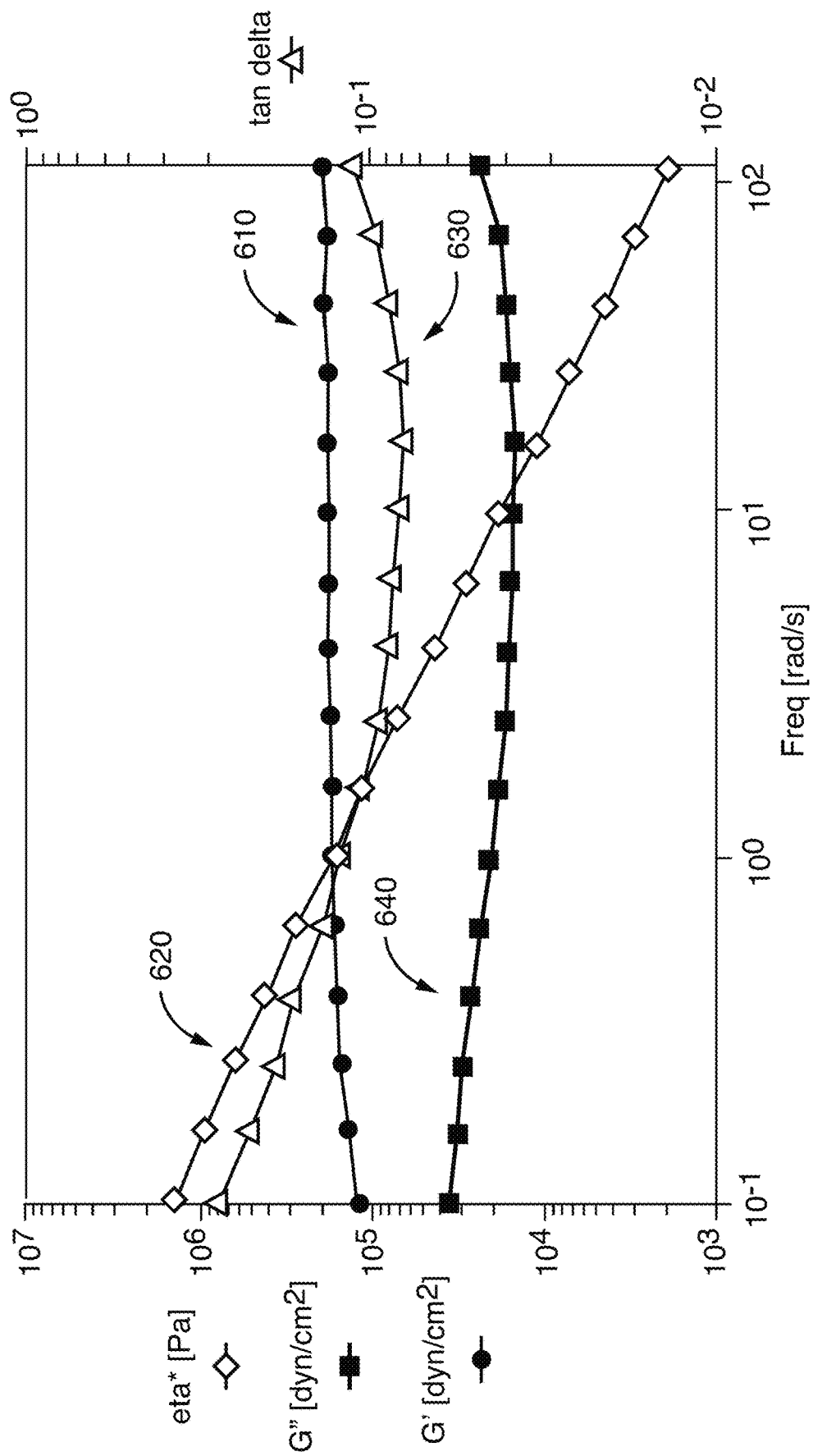
FIG. 6 illustrates shear dynamic mechanical properties as a function of frequency at ambient temperature for Algeness® DF (agarose based injectable). Algeness® DF gels show shear-thinning behavior and a predominance of solid like behavior like its comparator Voluma® XC. The Eta* data (620) for the agarose-based dermal fillers samples, however, are about 50 times higher than those observed tor Voluma® XC. The tan delta data (630) was obtained using elastic modulus data, G' (610) and loss modulus data, G" (640) presented in the figure.
Figure 7:
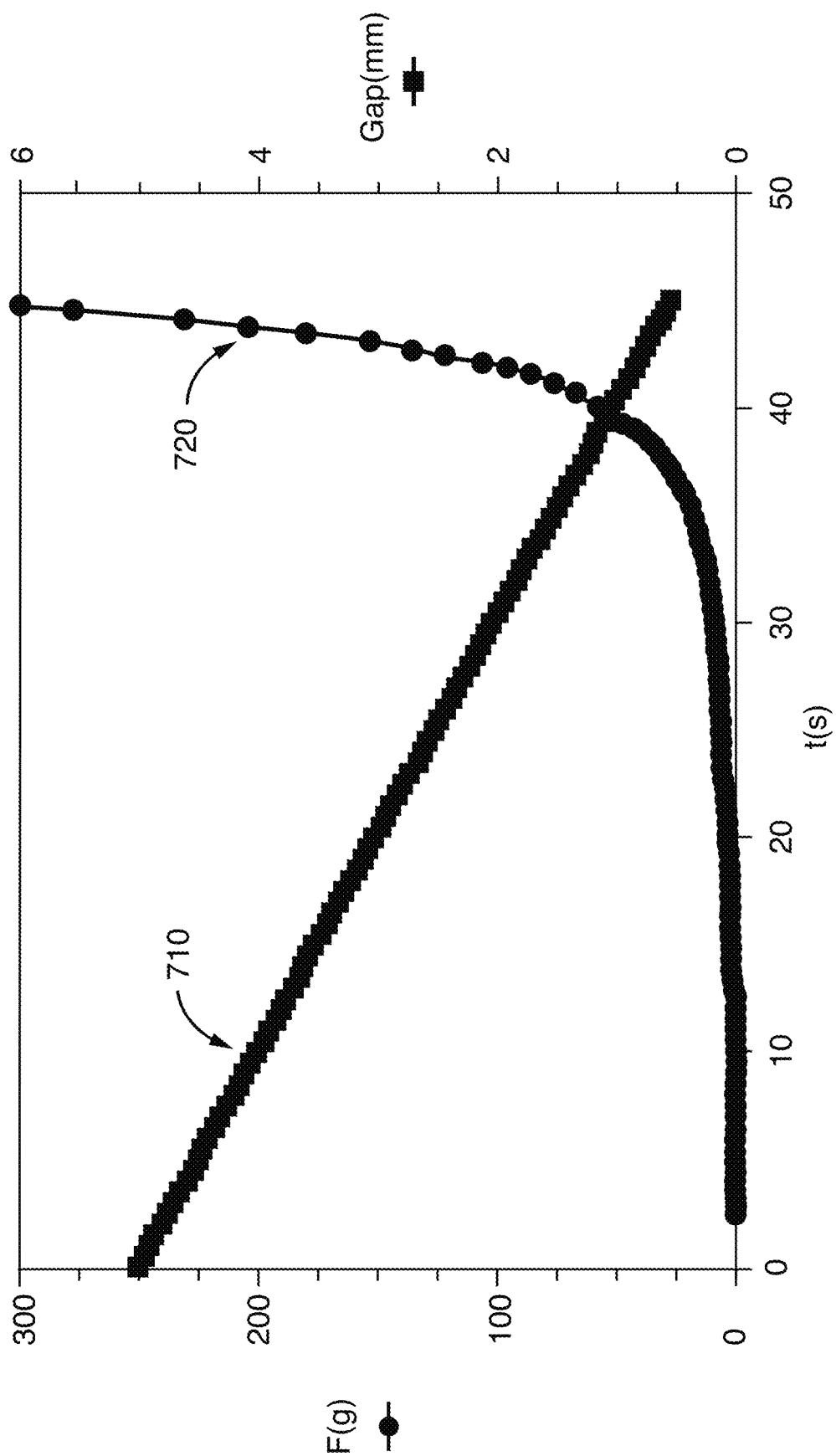
FIG. 7 illustrates force data (720) and parallel plate gap data (710) as a function of time during the compression of Voluma® XC at ambient temperature. The force data build relatively slowly with the first three mm of deformation and then increase sharply. The cross-sectional area of the gel is not constant during this experiment, but rather it increases as the sample is compressed.
Figure 8:
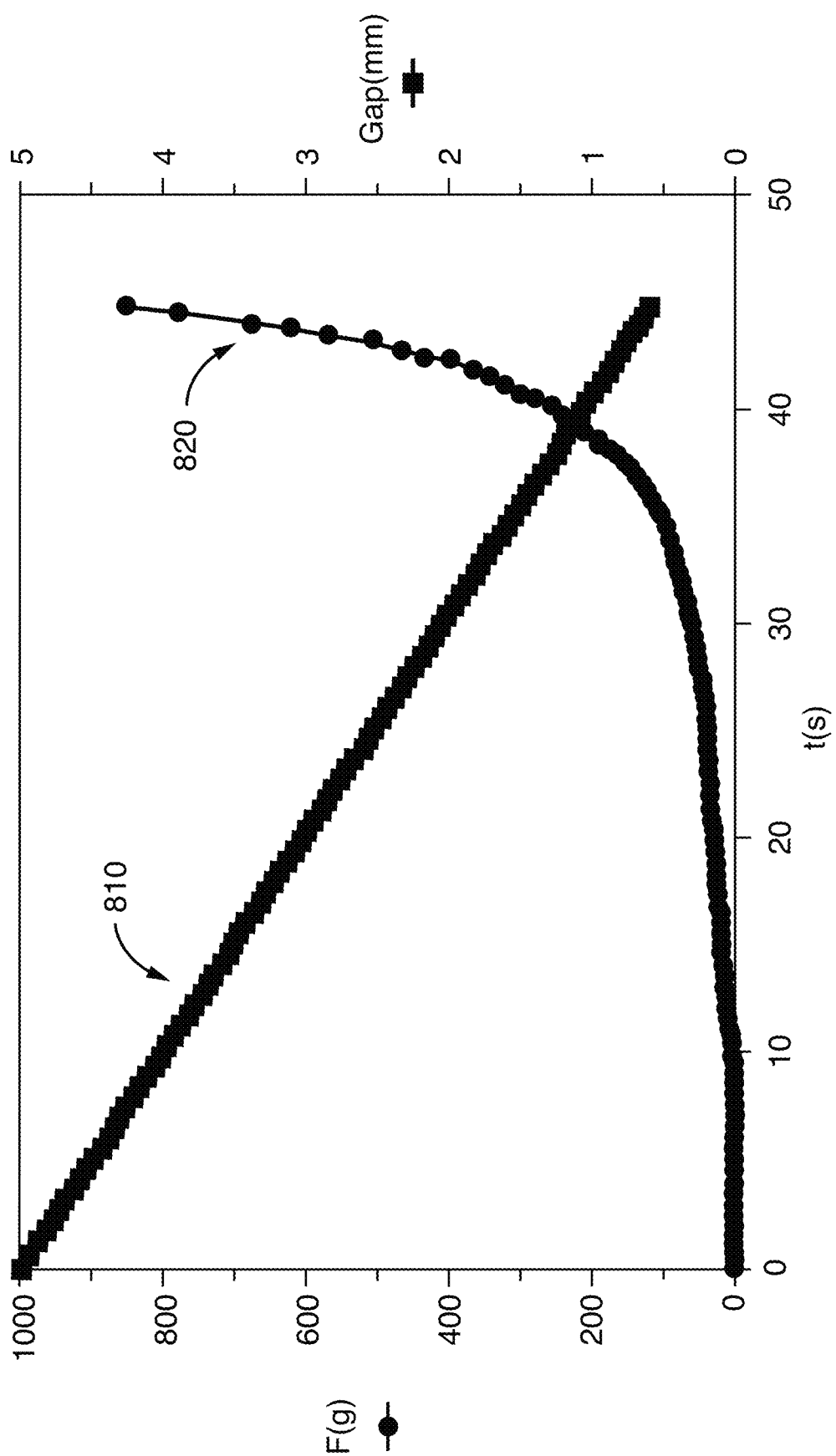
FIG. 8 illustrates force data (820) and parallel plate gap data (810) as a function of time during the compression of Algeness® DF at ambient temperature.

Rheometric testing showed that agarose gel filler had a significantly higher elastic modulus (G') and viscosity (G") than the crosslinked HA comparator. (Analytical Report is attached as Appendix A.) Both agarose gel filler and the crosslinked HA comparator demonstrated a decrease in viscosity that was proportional to applied force—a phenomenon known as shear thinning (FIG. 2 and FIG. 3). Agarose gel filler diluted 1:1 with normal saline showed a greater decrease in viscosity than the crosslinked HA filler diluted 1:1 with hyaluronidase. Viscosity decreased rapidly/almost instantaneously for both fillers and was maintained at the same low level over the ensuing 30-minute observation period (FIG. 4). Mathematical calculations of tan delta (G'/G") showed that both agarose gel filler and the crosslinked HA comparator had a predominance of solid over fluid behavior within the frequency range of testing (FIG. 5 and FIG. 6). Agarose gel filler and the crosslinked HA comparator had qualitatively similar responses to static compression testing (FIG. 7 and FIG. 8).

Discussion of Rheological Results

Based on these studies, agarose gel filler was found to have a rheological profile compatible with clinical behavior as a deep volumizer suitable for implantation in the subcutaneous or supraperiosteal tissue planes. Higher elasticity (G') indicates potential for greater tissue volumizing capacity and more volume-efficient filling. Higher viscosity indicates potential for greater contour stability and less spread of the filler after implantation. The shear thinning behavior demonstrated by agarose gel filler is typical also of crosslinked HA fillers, representing a controlled and predictable thinning of the gel associated with maintenance of its elastic properties within a physiologically relevant range of testing (linear viscoelastic range). Static compression testing is especially relevant for deep volumizers which are exposed to the weight of overlying tissues.

The rapid dispersion of agarose gel filler on mixing with saline, as evinced by instantaneous decrease in viscosity, correlates with in vitro testing showing dispersion of agarose gel filler with saline and gentle agitation. In contrast, HA filler under the same testing conditions takes up water hygroscopically and is not dispersed. Water uptake within the blood vessel lumen is understood to play a significant role in the occlusive potential of HA filler. This suggests that, under the right conditions, saline may be effective to disperse agarose gel filler without the need for enzymes or other additives. While rapid dispersion by saline provides an enhanced safety feature if a filler is inadvertently injected into a blood vessel, the effects of blood components that are not present in saline such as plasma proteins should also be taken into consideration. Further studies are now in progress with a particular focus on injectable safety.

EQUIVALENTS

It is understood that the detailed examples and embodiments described herein are given by way of example for illustrative purposes only. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A kit for performing a dermal filling procedure comprising:
   a) a filler container containing a marked fluid volume of an agarose-based filler; and
   b) a filler-dispersion container containing a marked fluid volume for saline; wherein the filler container and filler-dispersion container are each connectable to an injection needle and the marked fluid volume of the filler-dispersion container is within a ratio of 1:2 to 2:1 with the marked fluid volume of the filler container.

2. The kit of claim 1, wherein fluid volume of the filler container is between about 0.7 mL and about 3 mL.

3. The kit of claim 1, further comprising a second filler-dispersion container containing a marked fluid volume of saline, the second filler-dispersion container being equivalent to the filler-dispersion container.

4. The kit of claim 1, wherein the agarose-based filler is a biocompatible gel including between about 1% and 4% agarose.

5. The kit of claim 4, wherein the agarose-based filler includes between about 1% and 2% agarose.

6. The kit of claim 4, wherein the agarose-based filler includes between 0.1% and 0.6% hyaluronic acid.

7. The kit of claim 6, wherein the agarose-based filler includes between about 2% and 4% agarose and 0.3% and 0.6% hyaluronic acid.

8. The kit of claim 7, wherein the agarose-based filler includes about 3.5% agarose and about 0.4% hyaluronic acid.

9. The kit of claim 1, further comprising a heater that controls heating of the filler-dispersion container to substantially human body-temperature.

10. The kit of claim 1, further comprising a set of instructions to visually and physically inspect a patient to identify a lump or an undesired pocket of injected agarose-base filler between 1 minutes and 15 days after the injection of the filler container.

11. The kit of claim 10, wherein the set of instructions comprises visually and physically inspect a patient to identify a lump or an undesired pocket of injected agarose-base filler between 1 minutes and 30 minutes after injection of the filler container.

12. The kit of claim 10, further comprising instrucions to inject the filler-dispersion container at the location of the lump or the undesired pocket of injected agarose-based filler and to massage the location to remove the lump or the undesired pocket of injected agarose-based filler.

13. The kit of claim 1, further comprising a set of instructions to heat the saline within the filler-dispersion container to substantially human body temperature.

14. The kit of claim 1, wherein the filler container and the filler-dispersion container have substantially the same marked fluid volume.

15. The kit of claim 1, further comprising three or more filler-dispersion containers, each containing a marked fluid volume of saline.

16. A method of dispersing an injected agarose-based filler from a patient, the method comprising:
    identifying a lump or an undesired pocket of injected agarose-based filler under the patient's skin;
    injecting a first container of saline in an amount between about 0.7 mL to about 5 mL into the patient at the location of the lump or undesired pocket of injected agarose-base filler;
    massaging the location after injection ot disperse the lump or undesired pocket of injected agarose-base filler.

17. The method of claim 16, further comprising: heating the saline to approximate body temperature prior to injection.

18. The method of claim 16, further comprising: injecting a second container of saline in an amount between about 0.7 to about 5 mL into the patient at the location of the lump or undesired pocket of injected agarose-base filler.

19. The method of claim 18, wherein a first massage step occurs after the injection of the first container of saline and a second massaging step occurs after injecting the second container of saline.

20. The method of claim 16, further comprising: injecting a third container of saline in an amount between about 0.7 to about 5 mL into the patient at the location of the lump or undesired pocket of injected agarose-base filler.

21. The method of claim 16, wherein the injected agarose-based filler was injected into the patients 15 days or less prior to the identifying step.

22. The method of claim 16, wherein a fluid volume of saline contained in the first container is substantially equal to a fluid volume of injected agarose-based filler.

23. The method of claim 16, wherein a fluid volume of saline contained in the first vial is half of a fluid volume of injected agarose-based filler.

24. The method of claim 16, wherein a fluid volume of saline contained in the first container is twice a fluid volume of injected agarose-based filler.

25. A method of dispersing an injected agarose-based filler from a patient, wherein a lump or an undesired pocket of agarose-based filler is present under the patient's skin, the method comprising:
    injecting a first container of saline in an amount between about 0.7 mL to about 5 mL into the patient at the location of the lump or undesired pocket of injected agarose-based filler.

26. The method of claim 25, wherein the agarose-based filler is a biocompatible gel including between about 1% and 4% agarose.

27. The method of claim 26, wherein the agarose-based filler includes between about 1% and 2% agarose.

28. The method of claim 26, wherein the agarose-based filler further includes between 0.1% and 0.6% hyaluronic acid.

29. The method of claim 28, wherein the agarose-based filler includes between about 2% and 4% agarose and 0.3% and 0.6% hyaluronic acid.

30. The method of claim 25, further comprising: heating the saline to approximate body temperature prior to injection.

31. The method of claim 25, further comprising: injecting a second container of saline in an amount between about 0.7 to about 5 mL into the patient at the location of the lump or undesired pocket of injected agarose-base filler.

32. The method of claim 31, further comprising: injecting a third container of saline in an amount between about 0.7 to about 5 mL into the patient at the location of the lump or undesired pocket of injected agarose-base filler.

33. The method of claim 25, wherein the injected agarose-based filler was injected into the patients 15 days or less prior to the identifying step.

34. The method of claim 25, wherein a fluid volume of saline contained in the first container is substantially equal to a fluid volume or injected agarose-based filler.

35. The method of claim 25, wherein a fluid volume of saline contained in the first vial is half of a fluid volume of injected agarose-based filler.

36. The method of claim 25, wherein a fluid volume of saline container in the first container is twice a fluid volume of injected agarose-based filler.

* * * * *